(12) United States Patent
Noelke et al.

(10) Patent No.: US 8,779,220 B2
(45) Date of Patent: Jul. 15, 2014

(54) CAPTURE OF FLUORINATED VINYL MONOMERS USING IONIC LIQUIDS

(75) Inventors: Charles Joseph Noelke, Pinehurst, NC (US); Mark Brandon Shiflett, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/467,436

(22) Filed: May 9, 2012

(65) Prior Publication Data

US 2013/0123448 A1    May 16, 2013

Related U.S. Application Data

(60) Provisional application No. 61/484,360, filed on May 10, 2011.

(51) Int. Cl.
*C07C 17/38* (2006.01)
(52) U.S. Cl.
USPC ............ 570/177; 570/238; 570/262; 570/138
(58) Field of Classification Search
None
See application file for complete search history.

(56) References Cited

U.S. PATENT DOCUMENTS

| | | | | |
|---|---|---|---|---|
| 2,419,010 | A * | 4/1947 | Coffman et al. | ............... 526/227 |
| 3,193,539 | A | 7/1965 | Hauptschein | |
| 3,265,678 | A | 8/1966 | Hecht | |
| 7,544,813 | B2 | 6/2009 | Harmer et al. | |
| 2006/0197053 | A1 | 9/2006 | Shiflett et al. | |
| 2008/0028777 | A1 | 2/2008 | Boesmann et al. | |
| 2010/0144994 | A1 | 6/2010 | Shiflett et al. | |

FOREIGN PATENT DOCUMENTS

| | | |
|---|---|---|
| GB | 1094558 | 12/1967 |
| WO | 2005/113702 | 12/2005 |

OTHER PUBLICATIONS

Cheng, X. et al. "Absorption of vinyl chloride by room temperature ionic liquids" Clean, 2009, 37, 245-248.*
Zhang, S. et al. "Physical properties of ionic liquids: Database and evaluation" J. Phys. Chem. Ref. Data, 2006, 35, 1475-1517.*
Freemantle, Designer Solvents, Chemical and Engineering News, Mar. 30, 1998, pp. 32-37.
Lu et al., Advanced Applications of Ionic Liquids in Polymer Science, Progress in Polymer Science 34:431-448, 2009.
Haszeldine et al., Polymerization Studies Using Modified Ziegler-Natta Catalysts: 2 Polymerization of Vinyl Fluoride, Polymer, 1973, V. 14, 221-223.
Enderby, Ionic Liquids: Recent Progress and Remaining Problems, J. Phys. Condensed Matter, 5:(Supp 34B): B99-B106, 1993.
Gordon, Ionic Liquid Crystals: Hexafluorophosphate Salts, J Mater Chem, 1998, 8, pp. 2627-2636.
Welton, Room-Temperature Ionic Liquids Solvents for Synthesis and Catalysis, Chem. Rev. 1999, 99, pp. 2071-2083.
Slocum, Multipurpose High-Pressure Phase-Equilibrium Apparatus, Ind Eng Chem Fundam V14, No. 2, pp. 126-128,1975.

(Continued)

*Primary Examiner* — Fereydoun G Sajjadi
*Assistant Examiner* — Medhanit Bahta

(57) ABSTRACT

A method for capturing certain fluorinated vinyl monomers from a gaseous mixture using ionic liquids is described. The gaseous mixture is contacted with at least one ionic liquid, whereby at least a portion of the fluorinated vinyl monomer is absorbed by the ionic liquid. The method is useful for reducing emissions of fluorinated vinyl monomers and for increasing the product yields in the manufacture of polymers from these monomers.

12 Claims, 1 Drawing Sheet

(56) References Cited

OTHER PUBLICATIONS

Schotte, Collection of Phase Equilibrium Data for Separation Technology, Ind. Eng. Chem. Process Des. Dev. 1980, 19, pp. 432-439.

Seddon, Ionic Liquids for Clean Technology, J. Chem. Tech. Biotechnol., 1997, 68, pp. 351-356.

Bottaro, Recent Advances in Explosives and Solid Propellants, Chem Ind., 68, 1996.

* cited by examiner

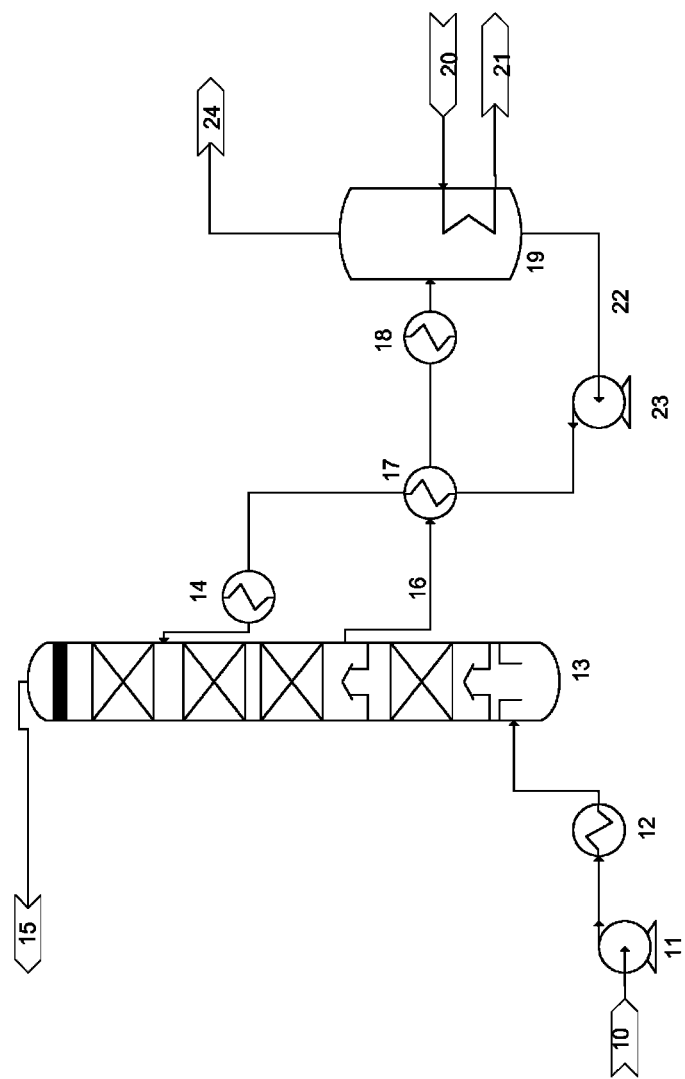

CAPTURE OF FLUORINATED VINYL MONOMERS USING IONIC LIQUIDS

This application claims priority under 35 U.S.C. §119(e) from, and claims the benefit of, U.S. Provisional Application No. 61/484,360, filed May 10, 2011, which is by this reference incorporated in its entirety as a part hereof for all purposes.

TECHNICAL FIELD

This invention relates to the field of ionic liquids. More specifically, this invention relates to a method for capturing certain fluorinated vinyl monomers using ionic liquids.

BACKGROUND

Fluorinated vinyl monomers, such as vinyl fluoride and vinylidene fluoride, are widely used to make polymers and copolymers that are useful in many applications. For example, poly(vinyl fluoride) finds wide use as a protective or decorative coating on substances such as cellulosics, flexible vinyls, plastics, rubbers and metals. Additionally, poly(vinyl fluoride) transparent film is used as the cover for solar plate collectors and photovoltaic cells. Poly(vinylidene fluoride) is used as a coating for metallic roofing, window frames, panel siding, and wire insulation.

The polymers and copolymers of fluorinated vinyl monomers are typically produced by free radical polymerization at high pressure. A problem in the manufacturing process of these polymers is that some of the monomer is vented to the atmosphere, resulting in product yield losses and environmental emissions.

A need thus remains for a method for capturing fluorinated vinyl monomers to increase production yields and reduce harmful emissions during the polymerization of these monomers.

SUMMARY

The subject matter disclosed herein addresses the stated need by providing a method for capturing certain fluorinated vinyl monomers using ionic liquids.

Accordingly, in one embodiment the disclosure hereof provides a method for capturing a fluorinated vinyl monomer from a gaseous mixture comprising the steps of:

a) providing a gaseous mixture comprising at least one fluorinated vinyl monomer selected from the group consisting of $C_2H_3F$, $C_2H_2F_2$, $C_2HF_3$, $C_3HF_5$, $C_3H_2F_4$, $C_3H_3F_3$, $C_3H_4F_2$, and $C_3H_5F$; and b) contacting the gaseous mixture with at least one ionic liquid whereby at least a portion of the fluorinated vinyl monomer is absorbed by the ionic liquid;

wherein an ionic liquid comprises an anion and a cation.

In certain alternative embodiments the cation of an ionic liquid can be selected from the group consisting of cations represented by the structures of the following formulae:

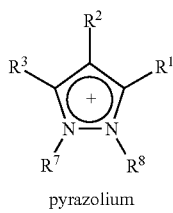

pyrazolium

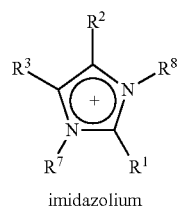

imidazolium

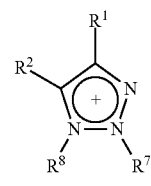

1,2,3-triazolium

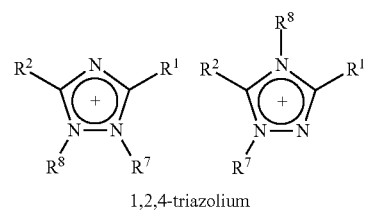

1,2,4-triazolium

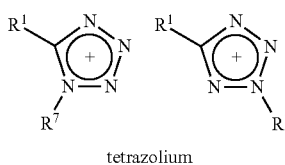

tetrazolium

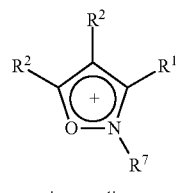

isoxazolium

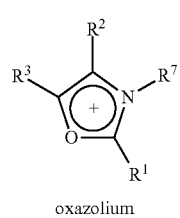

oxazolium

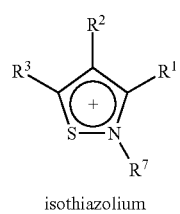

isothiazolium

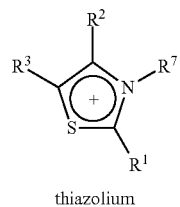

thiazolium

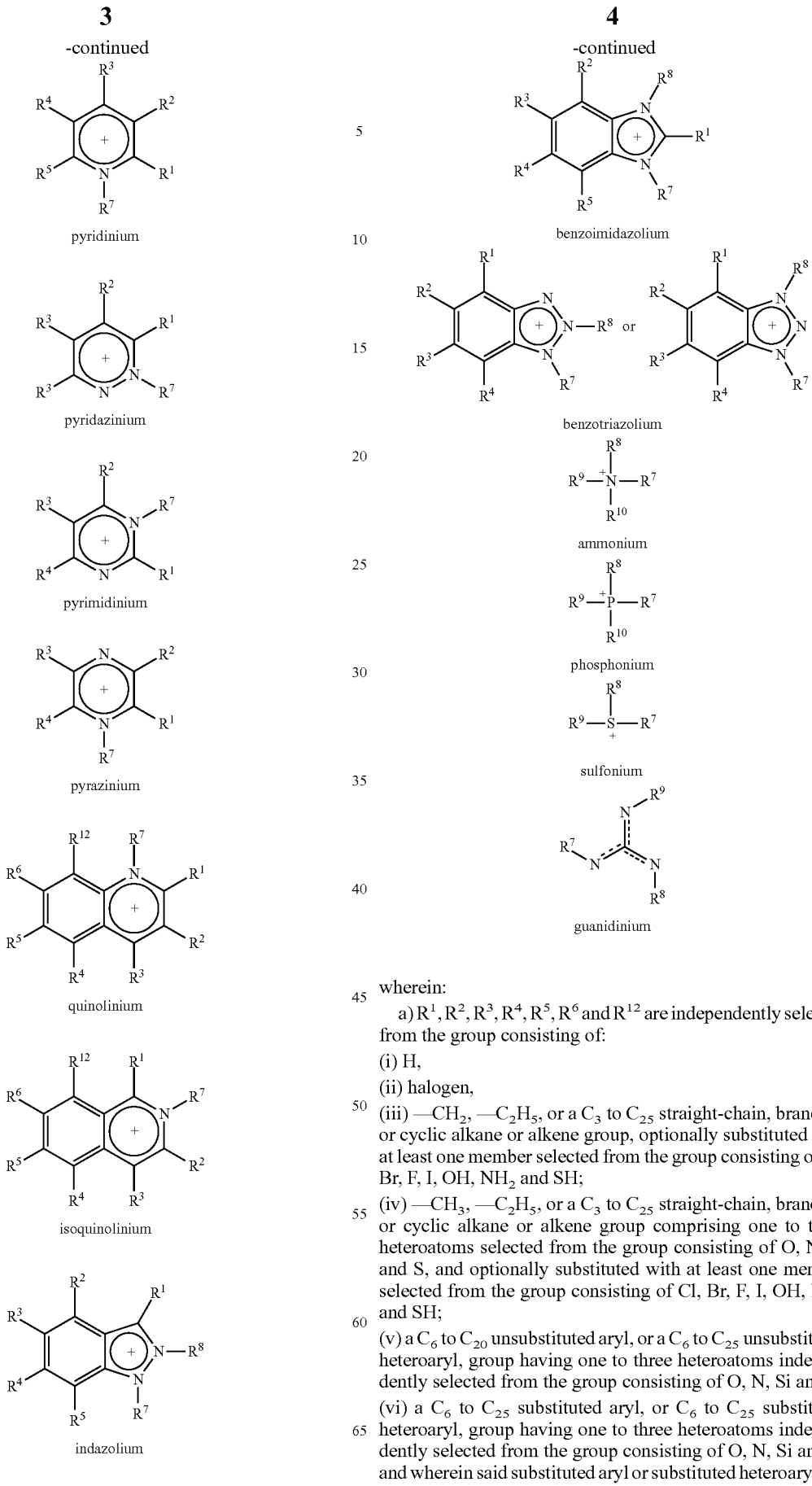

wherein:

a) $R^1, R^2, R^3, R^4, R^5, R^6$ and $R^{12}$ are independently selected from the group consisting of:

(i) H, (ii) halogen, (iii) —CH$_2$, —C$_2$H$_5$, or a C$_3$ to C$_{25}$ straight-chain, branched or cyclic alkane or alkene group, optionally substituted with at least one member selected from the group consisting of Cl, Br, F, I, OH, NH$_2$ and SH;

(iv) —CH$_3$, —C$_2$H$_5$, or a C$_3$ to C$_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, NH$_2$ and SH;

(v) a C$_6$ to C$_{20}$ unsubstituted aryl, or a C$_6$ to C$_{25}$ unsubstituted heteroaryl, group having one to three heteroatoms independently selected from the group consisting of O, N, Si and S;

(vi) a C$_6$ to C$_{25}$ substituted aryl, or C$_6$ to C$_{25}$ substituted heteroaryl, group having one to three heteroatoms independently selected from the group consisting of O, N, Si and S; and wherein said substituted aryl or substituted heteroaryl has one to three substituents independently selected from the group consisting of:

(A) —$CH_3$, —$C_2H_5$, or $C_1$ to $C_{25}$ straight-chain, branched or cyclic alkane or alkene, optionally substituted with at least one member selected from the group consisting of Cl, Br, F, I, OH, $NH_2$ and SH, (B) OH, (C) $NH_2$, and (D) SH; and (vii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4;

b) $R^7$, $R^8$, $R^9$ and $R^{10}$ are independently selected from the group consisting of:

(viii) —$CH_3$, —$C_2H_5$, or $C_1$ to $C_{25}$ straight-chain, branched or cyclic alkane or alkene, optionally substituted with at least one member selected from the group consisting of Cl, Br, F, I, OH, $NH_2$ and SH;

(ix) —$CH_3$, —$C_2H_5$, or $C_1$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;

(x) a $C_6$ to $C_{25}$ unsubstituted aryl, or $C_6$ to $C_{25}$ unsubstituted heteroaryl, group having one to three heteroatoms independently selected from the group consisting of O, N, Si and S; and (xi) a $C_6$ to $C_{25}$ substituted aryl, or a $C_6$ to $C_{25}$ substituted heteroaryl, group having one to three heteroatoms independently selected from the group consisting of O, N, Si and S; and wherein said substituted aryl or substituted heteroaryl group has one to three substituents independently selected from the group consisting of:

(E) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH, (F) OH, (G) $NH_2$, and (H) SH; and (xii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4; and c) optionally at least two of $R^1$, $R^2$, $R^3$, $R^4$, $R^5$, $R^6$, $R^7$, $R^8$, $R^9$ and $R^{10}$ can together form a cyclic or bicyclic alkanyl or alkenyl group.

BRIEF DESCRIPTION OF THE DRAWING

FIG. 1 is a flow diagram of an exemplary system for use in the capture of fluorinated vinyl monomers using the method described herein.

DETAILED DESCRIPTION

As used above and throughout the description of the methods hereof, the following terms, unless otherwise indicated, shall be defined as follows:

The term "ionic liquid" refers to an organic salt that is fluid at or below about 100° C.

The term "fluorinated vinyl monomer" as used herein, refers to a vinyl compound containing 2 or 3 carbon atoms selected from the group consisting of $C_2H_3F$, $C_2H_2F_2$, $C_2HF_3$, $C_3HF_5$, $C_3H_2F_4$, $C_3H_3F_3$, $C_3H_4F_2$, and $C_3H_5F$. Exemplary fluorinated vinyl compounds include without limitation HFC=$CH_2$ (vinyl fluoride), HFC=CHF, $H_2C$=$CF_2$ (vinylidene fluoride), and HFC=CH—$CH_3$.

The term "gaseous mixture", as used herein, refers to a mixture of gases containing at least one fluorinated vinyl monomer. The gaseous mixture may contain other gases such as nitrogen and water vapor. The gaseous mixture may, for example, be the emissions resulting from the manufacture of a polymer or copolymer using a fluorinated vinyl monomer.

The terms "capture" and "capturing", as used herein, refer to the removal of at least a portion of a fluorinated vinyl monomer from a gaseous mixture by absorption into an ionic liquid.

Disclosed herein is a method for capturing certain fluorinated vinyl monomers from a gaseous mixture using ionic liquids. The method is useful for reducing emissions of fluorinated vinyl monomers and for increasing the product yields in the manufacture of polymers from these monomers. The method disclosed herein provides a relatively simple, low cost way to achieve these stated benefits.

Ionic Liquids

Ionic liquids suitable for use as disclosed herein can, in principle, be any ionic liquid that absorbs fluorinated vinyl monomers; however, ionic liquids that have minimal absorption of fluorinated vinyl monomers will, while still useful, be somewhat less effective. Ideally, ionic liquids having high absorption of fluorinated vinyl monomers are desired for use as described herein to obtain a greater efficiency of operation. Additionally, mixtures of two or more ionic liquids may be used.

Many ionic liquids are formed by reacting a nitrogen-containing heterocyclic ring, preferably a heteroaromatic ring, with an alkylating agent (for example, an alkyl halide) to form a cation. Examples of suitable heteroaromatic rings include substituted pyridines and imidazoles. These rings can be alkylated with virtually any straight, branched or cyclic $C_{1-20}$ alkyl group, but preferably, the alkyl groups are $C_{1-16}$ groups. Various other cations such as ammonium, phosphonium, sulfonium, and guanidinium may also be used for this purpose.

Ionic liquids suitable for use herein may also be synthesized by salt metathesis, by an acid-base neutralization reaction or by quaternizing a selected nitrogen-containing compound; or they may be obtained commercially from several companies such as Merck (Darmstadt, Germany), BASF (Mount Olive N.J.), Fluka Chemical Corp. (Milwaukee Wis.), and Sigma-Aldrich (St. Louis Mo.). For example, the synthesis of many ionic liquids is described by Shiflett et al in U.S. Patent Application Publication No. 2006/0 197 053, which is by this reference incorporated as a part hereof for all purposes.

Representative examples of ionic liquids suitable for use herein are included among those that are described in sources such as *J. Chem. Tech. Biotechnol.*, 68:351-356 (1997); *Chem. Ind.*, 68:249-263 (1996); *J. Phys. Condensed Matter*, 5: (supp 34B):B99-B106 (1993); *Chemical and Engineering News*, Mar. 30, 1998, 32-37; *J. Mater. Chem.*, 8:2627-2636 (1998); *Chem. Rev.*, 99:2071-2084 (1999); and WO 05/113, 702 (and references cited therein). In one embodiment, a library, i.e. a combinatorial library, of ionic liquids may be prepared, for example, by preparing various alkyl derivatives of a quaternary ammonium cation, and varying the associated anions.

Ionic liquids suitable for use herein comprise an anion and a cation. The cation is selected from the group consisting of cations represented by the structures of the following formulae:

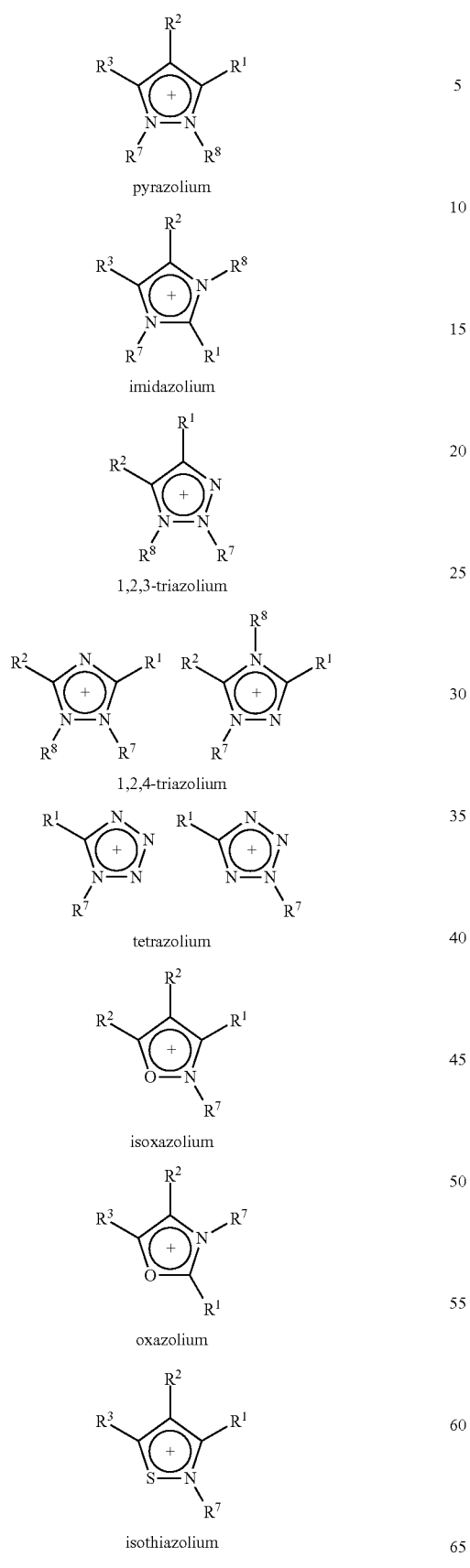

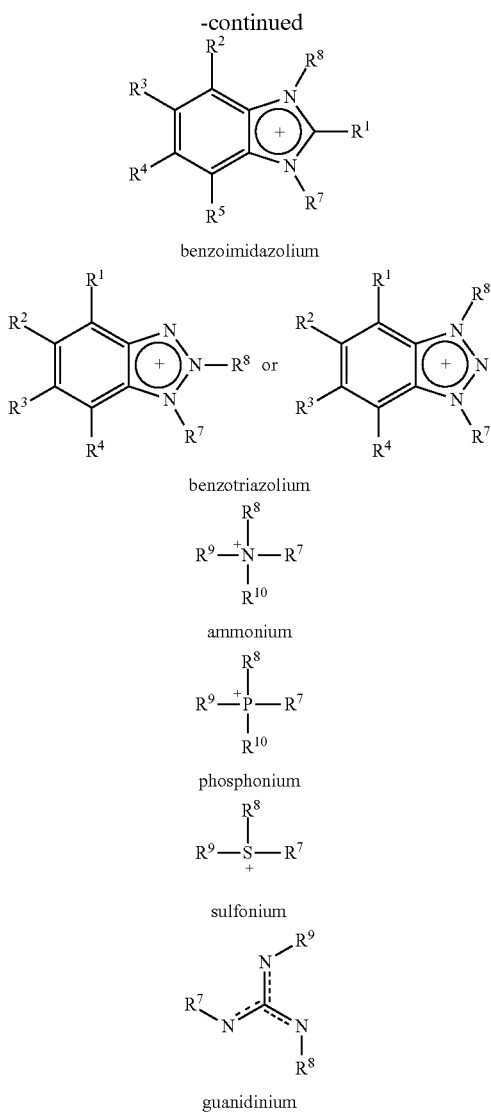

benzoimidazolium benzotriazolium ammonium phosphonium sulfonium guanidinium wherein:
a) $R^1$, $R^2$, $R^3$, $R^4$, $R^5$, $R^6$ and $R^{12}$ are independently selected from the group consisting of:
(i) H,
(ii) halogen,
(iii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(iv) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
(v) a $C_6$ to $C_{20}$ unsubstituted aryl, or a $C_6$ to $C_{25}$ unsubstituted heteroaryl, group having one to three heteroatoms independently selected from the group consisting of O, N, Si and S;
(vi) a $C_6$ to $C_{25}$ substituted aryl, or a $C_6$ to $C_{25}$ substituted heteroaryl, group having one to three heteroatoms independently selected from the group consisting of O, N, Si and S; and wherein said substituted aryl or substituted heteroaryl has one to three substituents independently selected from the group consisting of:
(A) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH,
(B) OH,
(C) $NH_2$, and
(D) SH; and
(vii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4;
b) $R^7$, $R^8$, $R^9$ and $R^{10}$ are independently selected from the group consisting of:
(viii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(ix) —$CH_3$, —$C_2H_5$, or a $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(x) a $C_6$ to $C_{25}$ unsubstituted aryl, or a $C_6$ to $C_{25}$ unsubstituted heteroaryl, group having one to three heteroatoms independently selected from the group consisting of O, N, Si and S; and $C_6$ to $C_{25}$ substituted aryl, or
(xi) a $C_3$ to $C_{25}$ substituted heteroaryl group having one to three heteroatoms independently selected from the group consisting of O, N, Si and S; and wherein said substituted aryl or substituted heteroaryl group has one to three substituents independently selected from the group consisting of:
(E) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH,
(F) OH,
(G) $NH_2$, and
(H) SH; and
(xii) —$(CH_2)_nSi(CH_2)_mCH_3$, —$(CH_2)_nSi(CH_3)_3$, or —$(CH_2)_nOSi(CH_3)_m$, where n is independently 1-4 and m is independently 0-4; and
c) optionally at least two of $R^1$, $R^2$, $R^3$, $R^4$, $R^5$, $R^6$, $R^7$, $R^8$, $R^9$ and $R^{10}$ can together form a cyclic or bicyclic alkanyl or alkenyl group.

In one embodiment, an ionic liquid as used herein can include an anion selected from one or more members of the group consisting of: $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_3]^{3-}$, $[HPO_3]^{2-}$, $[H_2PO_3]^{1-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, a fluorinated anion.

In one embodiment, an ionic liquid as used herein can include a fluorinated anion. Suitable fluorinated anions are described by Harmer et al (U.S. Pat. No. 7,544,813), and include without limitation 1,1,2,2-tetrafluoroethanesulfonate; 2-chloro-1,1,2-trifluoroethanesulfonate; 1,1,2,3,3,3-hexafluoropropanesulfonate; 1,1,2-trifluoro-2-(trifluoromethoxy)ethanesulfonate; 1,1,2-trifluoro-2-(pentafluoroethoxy)ethanesulfonate; 2-(1,2,2,2-tetrafluoroethoxy)-1,1,2,2-tetrafluoroethanesulfonate; 2-(1,1,2,2-tetrafluoroethoxy)-1,1,2,2-tetrafluoroethanesulfonate; 2-(1,1,2,2-tetrafluoro-2-iodoethoxy)-1,1,2,2-tetrafluoroethanesulfonate; 1,1,2,2-tetrafluoro-2-(pentafluoroethoxy)ethanesulfonate; N,N-bis(1,1,2,2-tetrafluoroethanesulfonyl)imide; and N,N-bis(1,1,2,3,3,3-hexafluoropropanesulfonyl)imide.

In one embodiment, an ionic liquid as used herein can include a cation selected from one or more members of the group consisting of pyridinium, pyridazinium, pyrimidinium, pyrazinium, imidazolium, pyrazolium, triazolium, oxazolium, triazolium, phosphonium, ammonium, and guanidinium.

In another embodiment, an ionic liquid as used herein can include an anion selected from one or more members of the group consisting of acetate, aminoacetate, ascorbate, benzoate, catecholate, citrate, dialkylphosphate, formate, fumarate, gallate, glycolate, glyoxylate, iminodiacetate, isobutyrate, kojate, lactate, levulinate, oxalate, pivalate, propionate, pyruvate, salicylate, succinamate, succinate, tiglate, tetrafluoroborate, tetrafluoroethanesulfonate, tropolonate, $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, $[BF_4]^-$, $[PF_6]^-$, $[SbF_6]$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, $F^-$, and anions represented by the structure of the following formula:

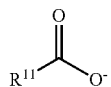

wherein $R^{11}$ is selected from the group consisting of:
(i) —$CH_2$, —$C_2H_5$, or a $C_3$ to $C_{17}$ straight-chain, branched or cyclic alkane or alkene group, optionally substituted with at least one member selected from the group consisting of Cl, Br, F, I, OH, $NH_2$ and SH;
(ii) —$CH_3$, —$C_2H_5$, or a $C_3$ to $C_{17}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
(iii) a $C_6$ to $C_{10}$ unsubstituted aryl, or a $C_6$ to $C_{17}$ unsubstituted heteroaryl, group having one to three heteroatoms independently selected from the group consisting of O, N, Si and S; and
(iv) a $C_6$ to $C_{10}$ substituted aryl, or a $C_6$ to $C_{17}$ substituted heteroaryl, group having one to three heteroatoms independently selected from the group consisting of O, N, Si and S; and wherein said substituted aryl or substituted heteroaryl has one to three substituents independently selected from the group consisting of:
(A) —$CH_3$, —$C_2H_5$, or a $C_3$ to $C_{17}$ straight-chain, branched or cyclic alkane or alkene, optionally substituted with at least one member selected from the group consisting of Cl, Br, F, I, OH, $NH_2$ and SH,
(B) OH,
(C) $NH_2$, and
(D) SH.

In one embodiment, an ionic liquid as used herein is selected from one or more members of the group consisting of 1-butyl-3-methylimidazolium dicyanimide, 1-butyl-3-methylimidazolium 1,1,2,3,3,3-hexafluoropropanesulfonate, 1-ethyl-3-methylimidazolium bis(trifluoromethylsulfonyl)imide, 1-butyl-3-methylpyridinium tetrafluoroborate, and 1-methyl-3-octylimidazolium 1,1,2,2-tetrafluoroethanesulfonate.

Method for Capturing Fluorinated Vinyl Monomers

One embodiment of the methods disclosed herein can be used to capture fluorinated vinyl monomer(s) from a gaseous mixture that contains the monomer, and/or to separate a fluorinated vinyl monomer from other components in a mixture containing the monomer, wherein such other components can be for example various fluids such as gases and/or liquids. One exemplary application of the method hereof, which is described below, is the capture of fluorinated vinyl monomers from emissions resulting from the manufacture of polymers from these monomers.

In one embodiment, the fluorinated vinyl monomer is selected from the group consisting of $C_2H_3F$, $C_2H_2F_2$, $C_2HF_3$, $C_3HF_5$, $C_3H_2F_4$, $C_3H_3F_3$, $C_3H_4F_2$, and $C_3H_5F$. In another embodiment, the fluorinated vinyl monomer is $HFC=CH_2$ (vinyl fluoride) or $H_2C=CF_2$ (vinylidene fluoride). In another embodiment, the fluorinated vinyl monomer is vinyl fluoride.

Polymerization of fluorinated vinyl monomers is typically done by free radical polymerization at high pressure. For example, poly(vinyl fluoride) can be produced by free radical polymerization of vinyl fluoride in an aqueous medium at a temperature between 50° C. and 150° C. and a pressure of 3.4 to 34.4 MPa using catalysts such as peroxides or azo compounds. Additionally, vinyl fluoride can be polymerized using a continuous process, as described in U.S. Pat. No. 3,265,678. Vinylidene fluoride can be polymerized in an aqueous medium using a variety of free radical initiators, such as, di-t-butyl peroxide (U.S. Pat. No. 3,193,539), peroxy dicarbonates and peroxy esters (GB 1,094,558), and disuccinic acid.

The emission from the polymerization process is, in various embodiments, a gaseous mixture containing primarily the fluorinated vinyl monomer, nitrogen, and water vapor. According to one embodiment of the method disclosed herein for capturing fluorinated vinyl monomers, the gaseous mixture is contacted with at least one ionic liquid, as described above, whereby at least a portion of the fluorinated vinyl monomer is absorbed by the ionic liquid. Ideally, substantially all (such as at least about 90 wt %, about 95 wt %, about 98 wt % or about 99 wt %) of the vinyl monomer is absorbed by the ionic liquid. Contacting of the fluorinated vinyl monomer with the ionic liquid may be done at atmospheric conditions of temperature and pressure. Alternatively, the gaseous mixture may be compressed and/or cooled before contact to increase capture of the fluorinated vinyl monomer by the ionic liquid.

The fluorinated vinyl monomer captured by the ionic liquid may be recovered and the ionic liquid regenerated in various ways. For example, the ionic liquid containing the absorbed fluorinated vinyl monomer may be heated in a stripping column to release the fluorinated vinyl monomer and regenerate the ionic liquid. Alternatively, the ionic liquid containing the absorbed fluorinated vinyl monomer may be regenerated using a flash technique in which the pressure is reduced and the ionic liquid is heated to release the absorbed fluorinated vinyl monomer, which may be recycled into the polymerization vessel. A further embodiment of the methods hereof is thus a method in which polymer is prepared from monomer that has been separated from an ionic liquid after it has been captured by the ionic liquid from a gaseous mixture.

An exemplary system for carrying out one embodiment of the method disclosed herein for capturing fluorinated vinyl monomers from emissions from polymer manufacturing using an ionic liquid is shown in FIG. 1. Referring to FIG. 1, the gas mixture from the manufacturing process 10 comprising the fluorinated vinyl monomer and other gases such as nitrogen and water vapor may be compressed by passage through compressor 11 and then cooled by a prechiller 12. The compressed and cooled gas mixture enters the bottom of absorption column 13, where it is contacted with the ionic liquid, whereby at least a portion of the fluorinated vinyl monomer is absorbed by the ionic liquid. The ionic liquid is cooled by precooler 14 before entry into the absorption column 13. The treated gas mixture 15, having at least a portion of the fluorinated vinyl monomer removed, is vented from the top of the absorption column 13.

The ionic liquid containing the absorbed fluorinated vinyl monomer 16 exits the absorption column 13 and enters a process heat exchanger 17. Next, the ionic liquid passes through a flash preheater 18 and enters flash tank 19. The flash tank is essentially a simple single stage stripper where the ionic liquid containing absorbed fluorinated vinyl monomer is regenerated by heating with steam 20. The condensate from the steam 21 exits the flash tank 19 and may be heated to regenerate the steam.

The regenerated ionic liquid 22 exits the bottom of the flash tank 19 and is pumped by recycle pump 23 back through the process heat exchanger 17 and cooled before entering the absorption column 13. Due to the very low vapor pressure of the ionic liquid, the flash tank vapor may contain only (or essentially only) fluorinated vinyl monomer 24 and, if so, a condenser is not required. The fluorinated vinyl monomer 24 exiting the flash tank 19 may be recycled into the reactor or collected for storage. When recycled into the reactor, the method can be extended to include a step of preparing polymer from the monomer that was previously captured from the gas mixture taken off from the original polymerization reaction.

EXAMPLES

This invention is further defined in the following examples. It should be understood that these examples, while indicating preferred aspects of the methods hereof, are given by way of illustration only. From the above discussion and these examples, the essential characteristics of the methods hereof can be ascertained, and without departing from the spirit and scope thereof, various changes and modifications these methods can be made to adapt them to other uses and conditions.

Solubility Measurements

Solubility measurements were made using a glass equilibrium cell (E. W. Slocum, *Ind. Eng. Chem. Fundam.* (1975) 14, 126). The glass equilibrium cell had a known volume and was agitated so that the upper phase (gas or liquid) mixed into the lower liquid phase. A known amount of ionic liquid was loaded into the cell and the cell was evacuated with heating to degas and remove any residual water in the ionic liquid. Knowing the density of the ionic liquid, the volume of the ionic liquid was calculated, and the difference from the initial glass cell volume was used to calculate the vapor space volume. A known amount of gas was fed into the cell and the temperature was held constant with a circulating oil bath. The pressure of the cell was measured and recorded. When the pressure was determined to no longer change, the cell was at equilibrium and the amount of gas absorbed was calculated by taking into account the amount of gas in the equilibrium cell vapor space. Further discussion of this equipment and procedure is available in W. Schotte, *Ind. Eng. Chem. Process Des. Dev.* (1980) 19, 432-439.

Example 1

Solubility of vinyl fluoride (VF) in 1-butyl-3-methylimidazolium dicyanimide ([bmim][dca])

A solubility study was made at temperatures of 24.81° C. and 100.03° C. over a pressure range from 0.1 to about 4.3 MPa where the solubilities ($x_{meas.}$) were measured using the glass equilibrium cell and method described above. Tables 1 and 2 provide data for temperature (T), pressure (P), and $x_{meas}$ at temperatures of 24.81° C. and 100.03° C., respectively.

TABLE 1

Solubility of Vinyl Fluoride in [bmim][dca] at 24.81° C.

| T (° C.) | P (MPa) | $x_{meas.}$ (mole fraction) |
|---|---|---|
| 24.81 | 0.1200 | 0.0259 |
| 24.81 | 0.3992 | 0.0822 |
| 24.81 | 0.6702 | 0.1333 |
| 24.81 | 1.0432 | 0.1994 |
| 24.81 | 1.4300 | 0.2629 |
| 24.81 | 1.7313 | 0.3091 |
| 24.81 | 1.9871 | 0.3470 |
| 24.81 | 2.2339 | 0.3824 |
| 24.81 | 2.4869 | 0.4175 |

TABLE 2

Solubility of Vinyl Fluoride in [bmim][dca] at 100.03° C.

| T (° C.) | P (MPa) | $x_{meas.}$ (mole fraction) |
|---|---|---|
| 100.03 | 0.4385 | 0.0289 |
| 100.03 | 0.9280 | 0.0583 |
| 100.03 | 1.3762 | 0.0854 |
| 100.03 | 1.9236 | 0.1152 |
| 100.03 | 2.3601 | 0.1381 |
| 100.03 | 2.8117 | 0.1601 |
| 100.03 | 3.3508 | 0.1845 |
| 100.03 | 3.7983 | 0.2033 |
| 100.03 | 4.2616 | 0.2214 |

Example 2

Solubility of vinyl fluoride (VF) in 1-butyl-3-methylimidazolium 1,1,2,3,3,3-hexafluoropropanesulfonate ([bmim][HFPS])

A solubility study was made at temperatures of 24.78° C. and 99.52° C. over a pressure range from 0.1 to about 3.7 MPa where the solubilities ($x_{meas.}$) were measured using the glass equilibrium cell and method described above. Tables 3 and 4 provide data for T, P, and $x_{meas}$ at temperatures of 24.78° C. and 99.52° C., respectively.

TABLE 3

Solubility of Vinyl Fluoride in [bmim][HFPS] at 24.78° C.

| T (° C.) | P (MPa) | $x_{meas.}$ (mole fraction) |
|---|---|---|
| 24.78 | 0.1124 | 0.0405 |
| 24.78 | 0.4413 | 0.1478 |
| 24.78 | 0.8350 | 0.2590 |

TABLE 3-continued

Solubility of Vinyl Fluoride in [bmim][HFPS] at 24.78° C.

| T (° C.) | P (MPa) | $x_{meas.}$ (mole fraction) |
|---|---|---|
| 24.78 | 1.1921 | 0.3487 |
| 24.78 | 1.5651 | 0.4345 |
| 24.78 | 1.9305 | 0.5132 |
| 24.78 | 2.2484 | 0.5796 |
| 24.78 | 2.4842 | 0.6301 |

TABLE 4

Solubility of Vinyl Fluoride in [bmim][HFPS] at 99.52° C.

| T (° C.) | P (MPa) | $x_{meas.}$ (mole fraction) |
|---|---|---|
| 99.52 | 0.5019 | 0.0574 |
| 99.52 | 0.9473 | 0.1042 |
| 99.52 | 1.3996 | 0.1475 |
| 99.52 | 1.8050 | 0.1836 |
| 99.52 | 2.2415 | 0.2199 |
| 99.52 | 2.6365 | 0.2508 |
| 99.52 | 3.1433 | 0.2869 |
| 99.52 | 3.7349 | 0.3257 |

Example 3

Solubility of vinyl fluoride (VF) in 1-ethyl-3-methylimidazolium bis(trifluoromethylsulfonyl)imide ([emim][Tf$_2$N])

A solubility study was made at temperatures of 4.83° C., 24.74° C. and 99.45° C. over a pressure range from 0.2 to about 4.2 MPa where the solubilities ($x_{meas.}$) were measured using the glass equilibrium cell and method described above. Tables 5, 6 and 7 provide data for T, P, and $x_{meas}$ at temperatures of 4.83° C., 24.74° C. and 99.45° C., respectively.

TABLE 5

Solubility of Vinyl Fluoride in [emim][Tf$_2$N] at 4.83° C.

| T (° C.) | P (MPa) | $x_{meas.}$ (mole fraction) |
|---|---|---|
| 4.83 | 0.1620 | 0.1020 |
| 4.83 | 0.3696 | 0.2142 |
| 4.83 | 0.5888 | 0.3171 |
| 4.83 | 0.8115 | 0.4106 |
| 4.83 | 1.0218 | 0.4914 |
| 4.83 | 1.2031 | 0.5580 |
| 4.83 | 1.3803 | 0.6222 |
| 4.83 | 1.5210 | 0.6729 |

TABLE 6

Solubility of Vinyl Fluoride in [emim][Tf$_2$N] at 24.74° C.

| T (° C.) | P (MPa) | $x_{meas.}$ (mole fraction) |
|---|---|---|
| 24.74 | 0.2613 | 0.1043 |
| 24.74 | 0.5185 | 0.1926 |
| 24.74 | 0.8646 | 0.2956 |
| 24.74 | 1.2328 | 0.3905 |
| 24.74 | 1.5217 | 0.4578 |
| 24.74 | 1.7602 | 0.5097 |
| 24.74 | 2.0215 | 0.5639 |

TABLE 6-continued

Solubility of Vinyl Fluoride in [emim][Tf$_2$N] at 24.74° C.

| T (° C.) | P (MPa) | $x_{meas.}$ (mole fraction) |
|---|---|---|
| 24.74 | 2.2546 | 0.6109 |
| 24.74 | 2.5083 | 0.6618 |

TABLE 7

Solubility of Vinyl Fluoride in [emim][Tf$_2$N] at 99.45° C.

| T (° C.) | P (MPa) | $x_{meas.}$ (mole fraction) |
|---|---|---|
| 99.45 | 0.4730 | 0.0594 |
| 99.45 | 0.9377 | 0.1130 |
| 99.45 | 1.3590 | 0.1569 |
| 99.45 | 1.6947 | 0.1894 |
| 99.45 | 2.0795 | 0.2238 |
| 99.45 | 2.4359 | 0.2538 |
| 99.45 | 2.8868 | 0.2892 |
| 99.45 | 3.4846 | 0.3317 |
| 99.45 | 4.2072 | 0.3773 |

Example 4

Solubility of vinyl fluoride (VF) in 1-butyl-3-methylpyridinium tetrafluoroborate ([bmPy][BF$_4$])

A solubility study was made at temperatures of 4.74° C., 24.80° C. and 100.03° C. over a pressure range from 0.1 to about 4.2 MPa where the solubilities ($x_{meas.}$) were measured using the glass equilibrium cell and method described above. Tables 8, 9 and 10 provide data for T, P, and $x_{meas}$ at temperatures of 4.74° C., 24.80° C. and 100.03° C., respectively.

TABLE 8

Solubility of Vinyl Fluoride in [bmPy][BF$_4$] at 4.74° C.

| T (° C.) | P (MPa) | $x_{meas.}$ (mole fraction) |
|---|---|---|
| 4.74 | 0.1248 | 0.0626 |
| 4.74 | 0.2910 | 0.1403 |
| 4.74 | 0.4330 | 0.2023 |
| 4.74 | 0.5792 | 0.2623 |
| 4.74 | 0.7508 | 0.3285 |
| 4.74 | 0.9308 | 0.3949 |
| 4.74 | 1.1204 | 0.4608 |
| 4.74 | 1.2990 | 0.5219 |
| 4.74 | 1.4417 | 0.5704 |

TABLE 9

Solubility of Vinyl Fluoride in [bmPy][BF$_4$] at 24.80° C.

| T (° C.) | P (MPa) | $x_{meas.}$ (mole fraction) |
|---|---|---|
| 24.80 | 0.1462 | 0.0470 |
| 24.80 | 0.4226 | 0.1281 |
| 24.80 | 0.7095 | 0.2041 |
| 24.80 | 1.0749 | 0.2916 |
| 24.80 | 1.3858 | 0.3595 |
| 24.80 | 1.6734 | 0.4181 |
| 24.80 | 1.9588 | 0.4732 |

TABLE 9-continued

Solubility of Vinyl Fluoride in [bmPy][BF$_4$] at 24.80° C.

| T (° C.) | P (MPa) | $x_{meas.}$ (mole fraction) |
|---|---|---|
| 24.80 | 2.2422 | 0.5255 |
| 24.80 | 2.4835 | 0.5689 |

TABLE 10

Solubility of Vinyl Fluoride in [bmPy][BF$_4$] at 100.03° C.

| T (° C.) | P (MPa) | $x_{meas.}$ (mole fraction) |
|---|---|---|
| 100.03 | 0.5474 | 0.0508 |
| 100.03 | 1.0246 | 0.0913 |
| 100.03 | 1.5810 | 0.1344 |
| 100.03 | 2.0022 | 0.1652 |
| 100.03 | 2.4394 | 0.1947 |
| 100.03 | 2.8379 | 0.2201 |
| 100.03 | 3.3157 | 0.2484 |
| 100.03 | 3.7266 | 0.2713 |
| 100.03 | 4.2272 | 0.2966 |

Example 5

Solubility of vinyl fluoride (VF) in 1-methyl-3-octylimidazolium 1,1,2,2-tetrafluoroethanesulfonate ([omim][TFES])

A solubility study was made at temperatures of 4.77° C., 24.82° C. and 100.04° C. over a pressure range from 0.1 to about 4.2 MPa where the solubilities ($x_{meas.}$) were measured using the glass equilibrium cell and method described above. Tables 11, 12 and 13 provide data for T, P, and $x_{meas}$ at temperatures of 4.77° C., 24.82° C. and 100.04° C., respectively.

TABLE 11

Solubility of Vinyl Fluoride in [omim][TFES] at 4.77° C.

| T (° C.) | P (MPa) | $x_{meas.}$ (mole fraction) |
|---|---|---|
| 4.77 | 0.1365 | 0.0833 |
| 4.77 | 0.3289 | 0.1867 |
| 4.77 | 0.4537 | 0.2483 |
| 4.77 | 0.5861 | 0.3098 |
| 4.77 | 0.7550 | 0.3829 |
| 4.77 | 0.9756 | 0.4719 |
| 4.77 | 1.1700 | 0.5457 |
| 4.77 | 1.3121 | 0.5999 |
| 4.77 | 1.4362 | 0.6485 |

TABLE 12

Solubility of Vinyl Fluoride in [omim][TFES] at 24.82° C.

| T (° C.) | P (MPa) | $x_{meas.}$ (mole fraction) |
|---|---|---|
| 24.82 | 0.1972 | 0.0785 |
| 24.82 | 0.4778 | 0.1778 |
| 24.82 | 0.8143 | 0.2812 |
| 24.82 | 1.1218 | 0.3651 |
| 24.82 | 1.3920 | 0.4326 |
| 24.82 | 1.7223 | 0.5088 |
| 24.82 | 1.9912 | 0.5676 |

TABLE 12-continued

Solubility of Vinyl Fluoride in [omim][TFES] at 24.82° C.

| T (° C.) | P (MPa) | $x_{meas.}$ (mole fraction) |
|---|---|---|
| 24.82 | 2.2725 | 0.6276 |
| 24.82 | 2.5414 | 0.6868 |

TABLE 13

Solubility of Vinyl Fluoride in [omim][TFES] at 100.04° C.

| T (° C.) | P (MPa) | $x_{meas.}$ (mole fraction) |
|---|---|---|
| 100.04 | 0.5185 | 0.0675 |
| 100.04 | 0.9935 | 0.1238 |
| 100.04 | 1.4734 | 0.1752 |
| 100.04 | 1.8285 | 0.2101 |
| 100.04 | 2.3249 | 0.2549 |
| 100.04 | 2.8193 | 0.2959 |
| 100.04 | 3.2585 | 0.3291 |
| 100.04 | 3.7052 | 0.3609 |
| 100.04 | 4.1589 | 0.3902 |

The results of these solubility studies indicate that ionic liquids are well suited for the job of capturing a fluorinated vinyl monomer from a gaseous mixture because of the solubility of the monomer therein.

What is claimed is:

1. A method for capturing a fluorinated vinyl monomer from a gaseous mixture comprising the steps of:
   a) providing a gaseous mixture comprising at least one fluorinated vinyl monomer selected from the group consisting of $C_2H_3F$, $C_2H_2F_2$, $C_2HF_3$, $C_3HF_5$, $C_3H_2F_4$, $C_3H_3F_3$, $C_3H_4F_2$, and $C_3H_5F$; and
   b) contacting the gaseous mixture with at least one ionic liquid, whereby at least a portion of the fluorinated vinyl monomer is absorbed by the ionic liquid;
   wherein said ionic liquid comprises a cation and an anion selected from one or more members of the group consisting of tetrafluoroethanesulfonate, [SbF$_6$]$^-$, [CF$_3$SO$_2$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$Cl]$^-$, [CF$_3$CO$_2$]$^-$, [CF$_3$OCFHCF$_2$SO$_3$]$^-$, [CF$_3$CF$_2$OCFHCF$_2$SO$_3$]$_-$, [CF$_3$CFHOCF$_2$CF$_2$SO$_3$]$_-$, [CF$_2$HCF$_2$OCF$_2$CF$_2$SO$_3$]$_-$, [CF$_2$ICF$_2$OCF$_2$CF$_2$SO$_3$]$_-$, [CF$_3$CF$_2$OCF$_2$CF$_2$SO$_3$]$_-$, [(CF$_2$HCF$_2$SO$_2$)$_2$N]$_-$, [(CF$_3$CFHCF$_2$SO$_2$)$_2$N]$_-$, F$_-$, and anions represented by the structure of the following formula:

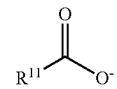

wherein R$^{11}$ is selected from the group consisting of:
(i) —CH$_3$, —C$_2$H$_5$, or C$_3$ to C$_{17}$ straight-chain, branched or cyclic alkane or alkene group substituted with F;
(ii) —CH$_3$, —C$_2$H$_5$, or C$_3$ to C$_{17}$ straight-chain, branched or cyclic alkane or alkene group comprising one to three heteroatoms selected from the group consisting of O, N, Si and S, and substituted with F; and
(iii) a C$_6$ to C$_{10}$ substituted aryl, or a C$_6$ to C$_{17}$ substituted heteroaryl group having one to three heteroatoms independently selected from the group consisting of O, N, Si and S; and substituted with —CH$_3$, —C$_2$H$_5$, or a C$_3$ to C$_{17}$ straight-chain, branched or cyclic alkane or alkene group substituted with F.
2. The method according to claim 1 wherein the cation is selected from the group consisting of cations represented by the structures of the following formulae:
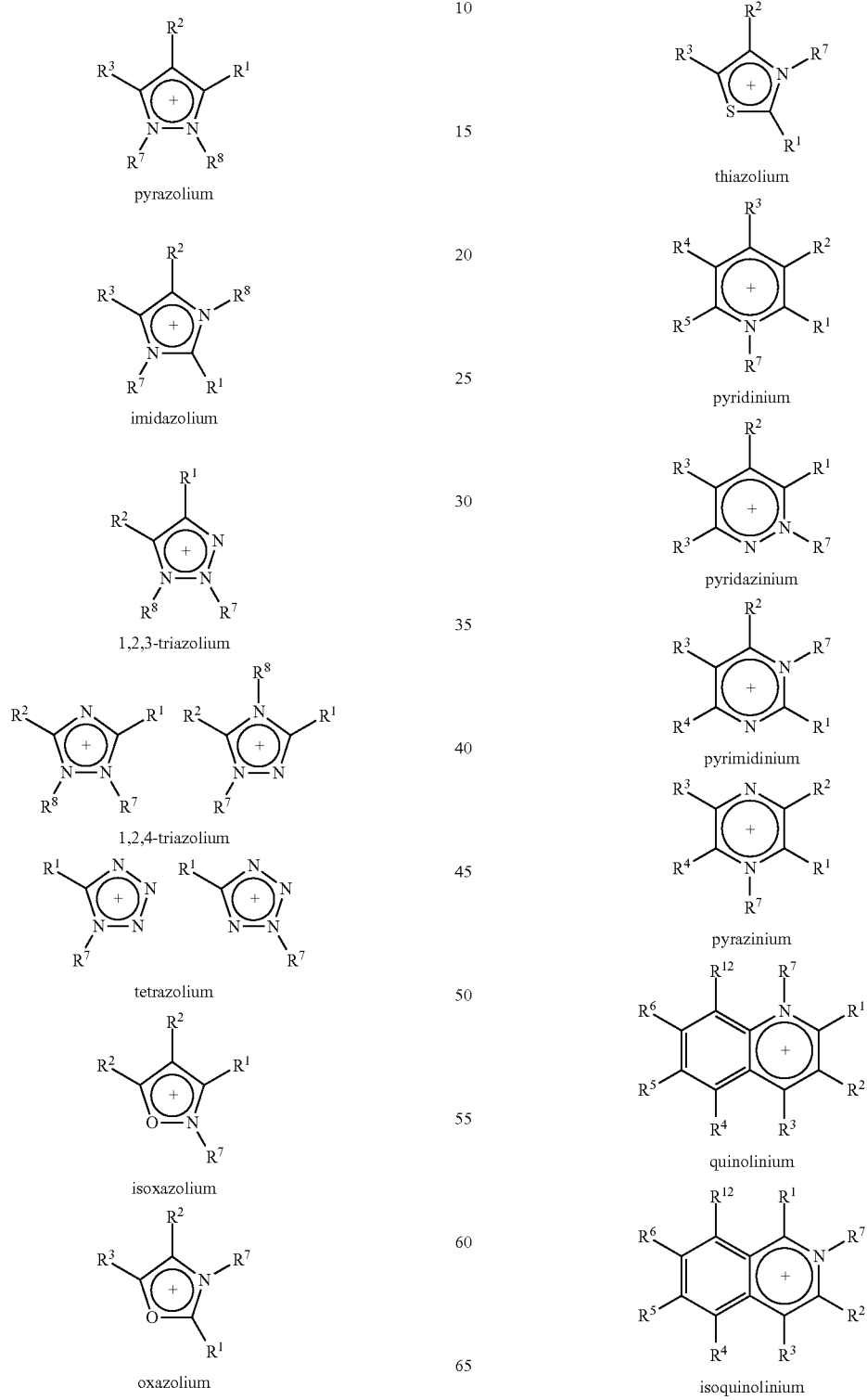

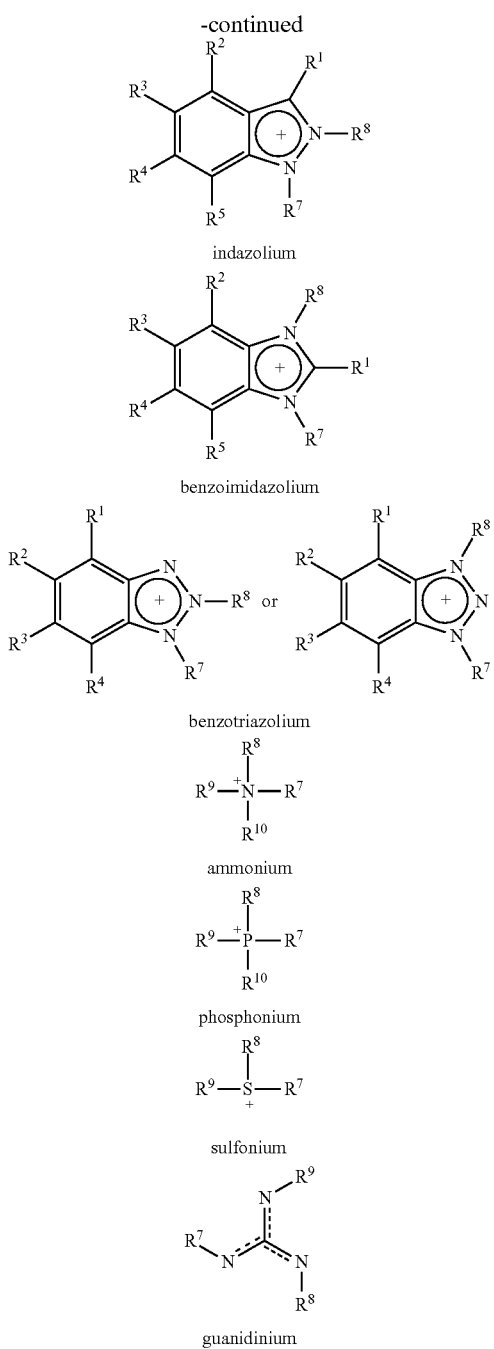

indazolium benzoimidazolium benzotriazolium ammonium phosphonium sulfonium guanidinium wherein:
(a) $R^1$, $R^2$, $R^3$, $R^4$, $R^5$, $R^6$, and $R^{12}$ are independently selected from the group consisting of:
 (i) H,
 (ii) halogen,
 (iii) —CH$_3$, —C$_2$H$_5$, or a C$_3$ to C$_{25}$ straight-chain, branched or cyclic alkane or alkene group, optionally substituted with at least one member selected from the group consisting of Cl, Br, F, I, OH, NH$_2$ and SH;
 (iv) —CH$_3$, —C$_2$H$_5$, or a C$_3$ to C$_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, NH$_2$ and SH;
 (v) a C$_6$ to C$_{20}$ unsubstituted aryl, or C$_6$ to C$_{25}$ unsubstituted heteroaryl, group having one to three heteroatoms independently selected from the group consisting of O, N, Si and S;
 (vi) a C$_6$ to C$_{25}$ substituted aryl, or a C$_6$ to C$_{25}$ substituted heteroaryl, group having one to three heteroatoms independently selected from the group consisting of O, N, Si and S; and wherein said substituted aryl or substituted heteroaryl has one to three substituents independently selected from the group consisting of:
  (A) —CH$_3$, —C$_2$H$_5$, or a C$_3$ to C$_{25}$ straight-chain, branched or cyclic alkane or alkene group, optionally substituted with at least one member selected from the group consisting of Cl, Br, F, I, OH, NH$_2$ and SH,
  (B) OH,
  (C) NH$_2$, and
  (D) SH; and
 (vii) —(CH$_2$)$_n$Si(CH$_2$)$_m$CH$_3$, —(CH$_2$)$_n$Si(CH$_3$)$_3$, or —(CH$_2$)$_n$OSi(CH$_3$)$_m$, where n is independently 1-4 and m is independently 0-4;
(b) $R^7$, $R^8$, $R^9$, and $R^{10}$ are independently selected from the group consisting of:
 (i) —CH$_3$, —C$_2$H$_5$, or a C$_3$ to C$_{25}$ straight-chain, branched or cyclic alkane or alkene group, optionally substituted with at least one member selected from the group consisting of Cl, Br, F, I, OH, NH$_2$ and SH;
 (ii) —CH$_3$, —C$_2$H$_5$, or a C$_3$ to C$_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, NH$_2$ and SH;
 (iii) a C$_6$ to C$_{25}$ unsubstituted aryl, or a C$_6$ to C$_{25}$ unsubstituted heteroaryl, group having one to three heteroatoms independently selected from the group consisting of O, N, Si and S; and
 (iv) a C$_6$ to C$_{25}$ substituted aryl, or a C$_6$ to C$_{25}$ substituted heteroaryl, group having one to three heteroatoms independently selected from the group consisting of O, N, Si and S; and wherein said substituted aryl or substituted heteroaryl group has one to three substituents independently selected from the group consisting of:
  (A) —CH$_3$, —C$_2$H$_5$, or a C$_3$ to C$_{25}$ straight-chain, branched or cyclic alkane or alkene group, optionally substituted with at least one member selected from the group consisting of Cl, Br, F, I, OH, NH$_2$ and SH,
  (B) OH,
  (C) NH$_2$, and
  (D) SH; and
 (v) —(CH$_2$)$_n$Si(CH$_2$)$_m$CH$_3$, —(CH$_2$)$_n$Si(CH$_3$)$_3$, or —(CH$_2$)$_n$OSi(CH$_3$)$_m$,
where n is independently 1-4 and m is independently 0-4; and
(c) optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group.

3. The method according to claim 1 wherein the gaseous mixture is compressed or cooled.

4. The method according to claim 1 wherein the fluorinated anion is selected from one or more members of the group consisting of
1,1,2,2-tetrafluoroethanesulfonate;
2-chloro-1,1,2-trifluoroethanesulfonate;
1,1,2,3,3,3-hexafluoropropanesulfonate;
1,1,2-trifluoro-2-(trifluoromethoxy)ethanesulfonate;
1,1,2-trifluoro-2-(pentafluoroethoxy)ethanesulfonate;
2-(1,2,2,2-tetrafluoroethoxy)-1,1,2,2-tetrafluoroethanesulfonate;

2-(1,1,2,2-tetrafluoroethoxy)-1,1,2,2-tetrafluoroethane-sulfonate;
2-(1,1,2,2-tetrafluoro-2-iodoethoxy)-1,1,2,2-tetrafluoro-ethanesulfonate;
1,1,2,2-tetrafluoro-2-(pentafluoroethoxy)ethanesulfonate;
N,N-bis(1,1,2,2-tetrafluoroethanesulfonyl)imide; and
N,N-bis(1,1,2,3,3,3-hexafluoropropanesulfonyl)imide.

5. The method according to claim 1 wherein the cation is selected from one or more members of the group consisting of pyridinium, pyridazinium, pyrimidinium, pyrazinium, imidazolium, pyrazolium, thiazolium, oxazolium, triazolium, phosphonium, ammonium, and guanidinium.

6. The method according to claim 1 wherein the fluorinated vinyl monomer is vinyl fluoride or vinylidene fluoride.

7. The method according to claim 6 wherein the fluorinated vinyl monomer is vinyl fluoride.

8. The method according to claim 1 wherein the ionic liquid is selected from one or more members of the group consisting of
1-butyl-3-methylimidazolium 1,1,2,3,3,3-hexafluoropropanesulfonate,
1-ethyl-3-methylimidazolium bis(trifluoromethylsulfonyl)imide, and
1-methyl-3-octylimidazolium 1,1,2,2-tetrafluoroethanesulfonate.

9. The method according to claim 1 further comprising the step of recovering the fluorinated vinyl monomer from the ionic liquid.

10. The method according to claim 9 further comprising the step of polymerizing the recovered fluorinated vinyl monomer.

11. The method of claim 1 wherein the ionic liquid is cooled.

12. The method of claim 1 wherein the gaseous mixture is contacted with a second ionic liquid that comprises an anion selected from one or more members of the group consisting of: $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_3]^-$, $[SO_4]^{2-}$, $[PO_3]^{3-}$, $[HPO_3]^{2-}$, $[H_2PO_3]^-$, $[PO_4]^{3-}$, $[HPO_4]^{2-}$, $[H_2PO_4]^-$, $[HSO_3]^-$, $[CuCl_2]^-$, Cl, Br, I, SCN, aminoacetate, ascorbate, benzoate, catecholate, citrate, dialkylphosphate, formate, fumarate, gallate, glycolate, glyoxylate, iminodiacetate, isobutyrate, kojate, lactate, levulinate, oxalate, pivalate, pyruvate, salicylate, succinamate, tiglate, tropolonate, and anions represented by the structure of the following formula:

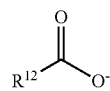

wherein $R^{12}$ is selected from the group consisting of:
(i) —$CH_3$, —$C_2H_5$, or $C_3$ to $C_{17}$ straight-chain, branched or cyclic alkane or alkene group, optionally substituted with at least one member selected from the group consisting of Cl, Br, I, OH, $NH_2$ and SH;
(ii) —$CH_3$, —$C_2H_5$, or $C_3$ to $C_{17}$ straight-chain, branched or cyclic alkane or alkene group comprising one to three heteroatoms selected from the group consisting of O, N, Si and S, and optionally substituted with at least one member selected from the group consisting of Cl, Br, I, OH, $NH_2$ and SH;
(iii) a $C_6$ to $C_{10}$ unsubstituted aryl, or a $C_6$ to $C_{17}$ unsubstituted heteroaryl group having one to three heteroatoms independently selected from the group consisting of O, N, Si and S; and
(iv) a $C_6$ to $C_{10}$ substituted aryl, or a $C_6$ to $C_{17}$ substituted heteroaryl group having one to three heteroatoms independently selected from the group consisting of O, N, Si and S; and wherein said substituted aryl or substituted heteroaryl has one to three substituents independently selected from the group consisting of:
(A) —$CH_3$, —$C_2H_5$, or a $C_3$ to $C_{17}$ straight-chain, branched or cyclic alkane or alkene group, optionally substituted with at least one member selected from the group consisting of Cl, Br, I, OH, $NH_2$ and SH,
(B) OH,
(C) $NH_2$, and
(D) SH.

* * * * *